United States Patent [19]

Georgi et al.

[11] Patent Number: 5,096,385
[45] Date of Patent: Mar. 17, 1992

[54] METHOD AND SYSTEM FOR UPSTREAM OCCLUSION DETECTION

[75] Inventors: Heinz W. Georgi, Rancho Santa Fe; Oliver J. Smith, Vista; Robert Butterfield, Poway, all of Calif.

[73] Assignee: IVAC Corporation, San Diego, Calif.

[21] Appl. No.: 433,627

[22] Filed: Nov. 8, 1989

[51] Int. Cl.$^5$ .................. F04B 43/12; F04B 49/02
[52] U.S. Cl. .................... 417/18; 417/474; 604/67
[58] Field of Search ............ 417/12, 18, 53, 63, 417/474; 604/67, 153

[56] References Cited

U.S. PATENT DOCUMENTS

| | | |
|---|---|---|
| 3,942,526 | 3/1976 | Wilder et al. . |
| 4,236,880 | 12/1980 | Archibald ............... 417/63 X |
| 4,373,525 | 2/1983 | Kobayashi .............. 417/63 |
| 4,394,862 | 7/1983 | Shim ..................... 604/67 |
| 4,394,862 | 7/1983 | Shim . |
| 4,526,574 | 7/1985 | Pekkarinen . |
| 4,530,696 | 7/1985 | Bisera et al. . |
| 4,563,179 | 1/1986 | Sakai . |
| 4,617,014 | 10/1986 | Cannon et al. ........... 604/ |
| 4,690,673 | 9/1987 | Bloomquist . |
| 4,702,675 | 10/1987 | Aldrovandi et al. ....... 417/63 |
| 4,710,163 | 12/1987 | Butterfield ............. 604/ |
| 4,747,828 | 5/1988 | Tseo . |
| 4,816,019 | 3/1989 | Kamen . |
| 4,836,752 | 6/1989 | Burkett ................. 417/474 X |
| 4,863,425 | 9/1989 | Slate et al. ............ 604/67 X |
| 4,950,235 | 8/1990 | Slate et al. ............ 604/67 X |

Primary Examiner—Leonard E. Smith
Attorney, Agent, or Firm—Fulwider Patton Lee & Utecht

[57] ABSTRACT

The method and system for detecting occlusion in a fluid line upstream of a pump concerns a fluid pump with a pump cycle in which the upstream pressure of the fluid line is communicated to the downstream portion of the fluid line. A pressure sensor located downstream of the pump is capable of measuring a relatively large negative-going pressure in the fluid line. A signal is generated to indicate occlusion based upon detection of negative-going pressure.

34 Claims, 9 Drawing Sheets

METHOD AND SYSTEM FOR UPSTREAM OCCLUSION DETECTION

BACKGROUND OF THE INVENTION

1. Field of the Invention

This invention relates generally to monitoring fluid flow, and more particularly relates to monitoring upstream occlusion in an intravenous fluid administration system utilizing an infusion pump.

2. Description of Related Art

Fluid delivery systems for infusing parenteral fluids are commonly used in hospitals, and typically include a bottle of parenteral fluid, an infusion pump, and an intravenous (IV) set including a tubing extending from the infusion pump to a cannula at the distal end of the tubing. Such infusion pumps provide a positive means for controlling the amount of fluid administered, and are an alternative to gravitational flow systems which are readily adapted to include a drip chamber for monitoring the amount of fluid administered, and occlusion situations in the system. Detection of upstream occlusions has typically been accomplished in infusion systems utilizing peristaltic pumps through the use of an optoelectric drop detector combined with a drip chamber. The drop detector senses the occlusion by detecting the absence of drops, which may be due to a clamped or kinked upstream tubing, as well as an empty IV fluid container.

There is a need in the medical industry for elimination of such drop detectors in connection with IV infusion pump systems. An upstream occlusion can simply be detected by addition of an upstream pressure transducer, but this alternative adds considerable cost to both the instrument and the disposable portion of the IV administration set.

One solution to this problem has been to incorporate a pressure transducer in the infusion pump itself. In one such device a pressure transducer is placed in the middle of the pumping area, allowing direct measurement of pressure in the tubing segment, which is indicative of the inlet pressure. However, it would be desirable to permit detection of upstream occlusion in an intravenous fluid administration system utilizing a peristaltic pump without requiring modifications to the disposable set or the pumping mechanism itself. The present invention addresses these needs.

SUMMARY OF THE INVENTION

The present invention provides a method and a system for detecting occlusion in a fluid line upstream of a pump adapted to cause fluid to flow from an upstream portion to a downstream portion of the fluid line, the pump having a cycle with a period during which fluid pressure is communicated from the upstream portion to the downstream portion of the fluid line. Fluid pressure is monitored in the fluid line downstream of the pump to detect the occurrence of a negative-going pressure transient, and a signal is generated indicating an occlusion when negative-going pressure transient is detected.

In a preferred embodiment, a plurality of samples of pressure measurements are taken, the difference between two downstream fluid pressure measurements which are a predetermined sampling interval apart within each measurement cycle is determined, the difference is compared with a difference threshold value, and the occlusion signal is generated when the difference exceeds this difference threshold value. In another embodiment, a downstream fluid pressure parameter is based upon the power content of the pressure waveform over a predetermined range of frequencies. This parameter is compared with a power level threshold and the occlusion signal is generated when the parameter exceeds this power level threshold.

Artifacts may also be detected and their existence used to inhibit the generation of false occlusion alarms. Sampling of the downstream pressure is initiated prior to the time of communication of the upstream pressure to the downstream pressure and if pressure below a predetermined threshold is measured, or if the pressure is changing in excess of a predetermined threshold, the generation of an occlusion alarm can be inhibited. In the case of severe artifacts causing gross pressure changes, a subsequent occlusion alarm may be considered to be unreliable and during that pump cycle it can be inhibited.

Other aspects and advantages of the invention will become apparent from the following detailed description and the accompanying drawings, illustrating by way of example the features of the invention.

DETAILED DESCRIPTION OF THE PREFERRED EMBODIMENT

As is shown in the drawings for purposes of illustration, the invention is embodied in a method and a system for monitoring upstream occlusion in an IV administration set based upon downstream pressure measurements. According to the currently preferred mode of the invention, a pressure measurement is taken at the beginning of a predefined detection window in a period of the pump cycle. Thereafter the downstream fluid pressure is sampled periodically for the rest of the detection period. With every new sample taken a test is performed for possible upstream occlusion. This test involves three values: the first sample taken at the beginning of the detection window, the present sample and the sample a given time period (10 ms) before the present sample. If the first pressure sample is above a given threshold (minus 120 mmHg) and the present pressure sample is below a given threshold (minus 30 mmHg) and the negative pressure difference between the present sample and the sample the given time period (10 ms) before the present sample exceeds another threshold (more than −60 mmHg) an occlusion has been detected. If the first pressure sample is below the threshold (minus 120 mmHg) an artifact condition is detected and a possible occlusion cannot be detected during this particular period of cyclical transition in the flow cycle of the infusion pump. Thus, the method can also be used for preventing false alarms of upstream occlusion when an artifact such as would occur due to patient motion would otherwise indicate occlusion. In another embodiment of the invention, pressure measurements are taken continuously to determine the energy content during a predetermined period of the flow cycle of the pump, over a predetermined range of frequencies, to determine a downstream pressure parameter, and this parameter is compared with a threshold to identify upstream occlusion conditions. Since the pressure measurements can be taken downstream of the pump mechanism, the upstream occlusion monitoring system can be installed conveniently and at a minimum of expense in existing IV administration sets in which a downstream pressure sensor is already present for measurement of infusion pressures.

Referring now to FIGS. 1a-1e, a peristaltic pump generally encloses a pumping segment 10 of a fluid line 12, which is manipulated by peristaltic fingers to force fluid through the line. The most upstream peristaltic finger 14 moves to fully occlude the fluid line in the pumping segment. This marks the beginning of a period of non-flow in the flow cycle of the pump. The most downstream finger 16 disengages, allowing communication of fluid in the pumping segment between the most upstream finger 14 and the most downstream finger with the downstream portion of the fluid line. It has been observed that if the IV set is clamped off upstream of the pump, a relatively large negative-going pressure transient 18 may be detected by a pressure sensor located downstream during the cyclical flow transition period when the downstream finger opens the pump tubing to the downstream portion of the IV tubing which is generally connected to a patient. This negative-going pressure transient is caused by the vacuum 19 that is generated in the tubing when the flow of fluid into the pumping section of the tubing is restricted. When this vacuum is suddenly connected to the downstream side of the tubing, a detectable transient occurs in the pressure in the downstream fluid line.

Figure 1A:
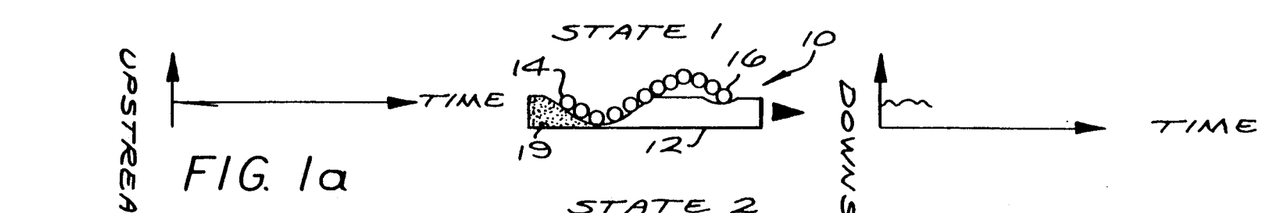
FIG. 1a, 1b, 1c, 1d and 1e illustrate sequential states of a peristaltic pump mechanism.
Figures 1B, 1C, 1D:
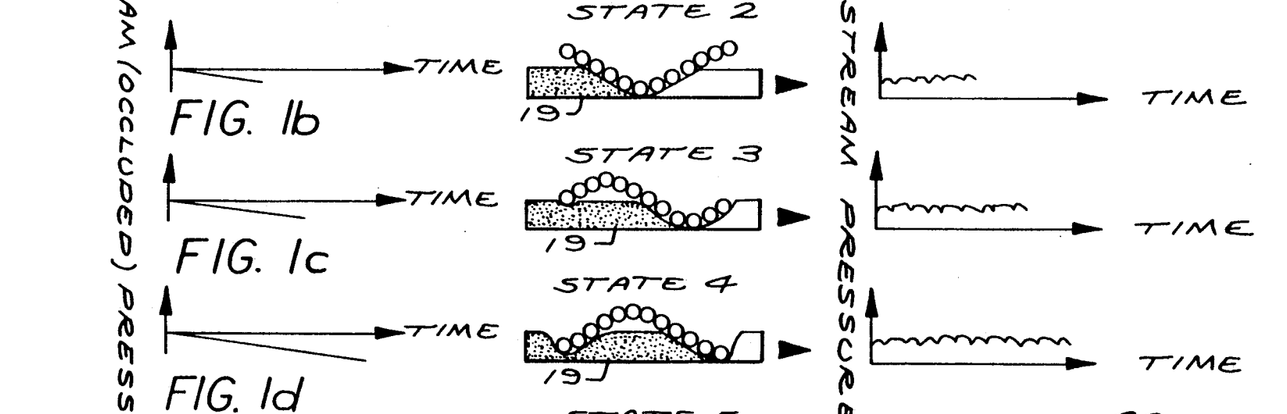
Figure 1E:
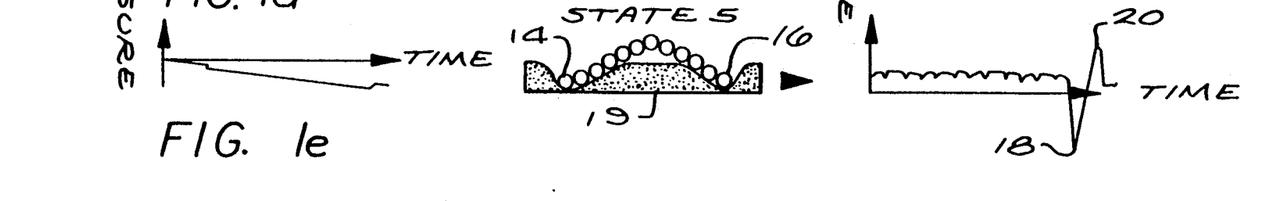

In FIGS. 1a-1e, the pumping mechanism is advancing fluid from the upstream portion of the line to the downstream portion of the line (left to right in the diagram). Upstream pressures are shown on the left of the pumping segment illustration, and downstream pressures are shown on the right side of the pumping segment illustrations. A total occlusion exists in the upstream line. In FIGS. 1a to 1d an increasing partial vacuum is generated by the displacement of the pumping mechanism. When the vacuum generated during the states shown in FIGS. 1a-1d is suddenly connected to the pressure transducer located in the downstream tubing, the output signal of the pressure transducer drops very sharply as is shown in FIG. 1e. Since downstream fluid impedance is typically low, a small amount of fluid is drawn backward allowing the tubing walls downstream of the most upstream finger 14 to return to their original dimensions. This allows the pressure to rise again until it reaches static conditions. The rate of this equalization and the shape of this pressure transient depends on the downstream fluid impedance determined by the IV set, filters, cannula, and the patient. The pressure may overshoot if the recovery is fast enough, causing the mass of the fluid column to oscillate with the compliance of the tubing. The initial negative pressure-going transient 18 is shown in FIG. 1e, and the positive pressure transient 20 may help distinguish the negative-going pressure transient sufficiently so that an occlusion is readily identifiable.

A well known feature of a conventional peristaltic pump is its non-uniform flow rate over each cycle, with an actual non-flow period typically over 25 percent of the duty cycle of the pump. This cyclical flow transition period may be minimized in the pump by operating the stepper motor which drives the pump at its maximum rate during the transition phase. It is in this so-called "speed up" time period where the pinch-off point of the pumping fingers switches from downstream to upstream, opening the pump tubing to the downstream portion of the IV tubing leading to the pressure transducer and the patient. The increase in speed of the motor is synchronized by a rotation sensor, such as a rotating disk which rotates in correlation with the rotation of the cam mechanism of the pump, and which bears one or more detectable flags. This switching of pinch-off point from downstream to upstream thereby communicating the upstream pressure to the downstream pressure permits the definition of a detection "window" where the negative-going transient will occur when there is occlusion upstream of the pump. This narrow window reduces susceptibility of the upstream occlusion detection system to artifact transients, which may, for example, be caused by movement of the IV tubing.

Figure 2:
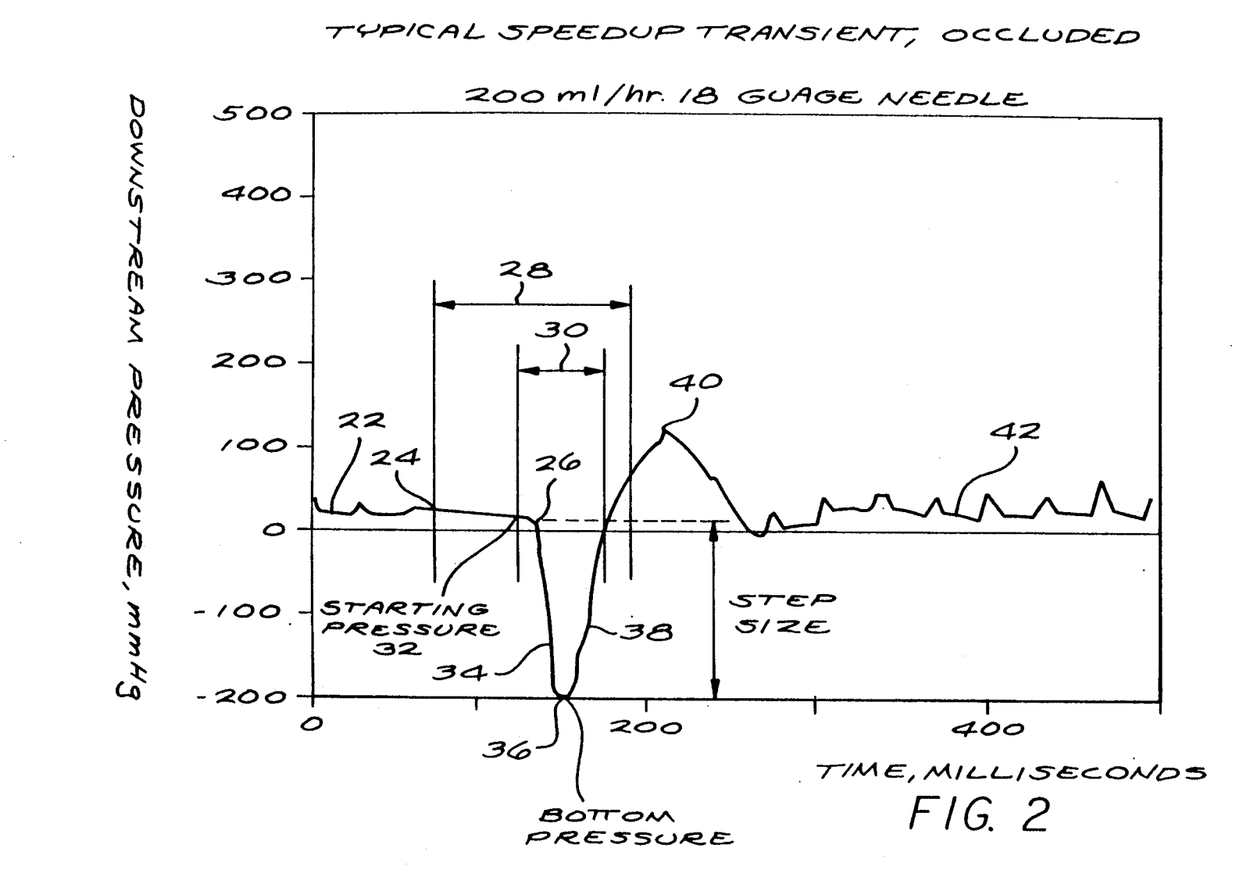
FIG. 2 illustrates a typical downstream pressure waveform indicating an upstream occlusion during the period of non-flow of a peristaltic pump.
Figure 3:
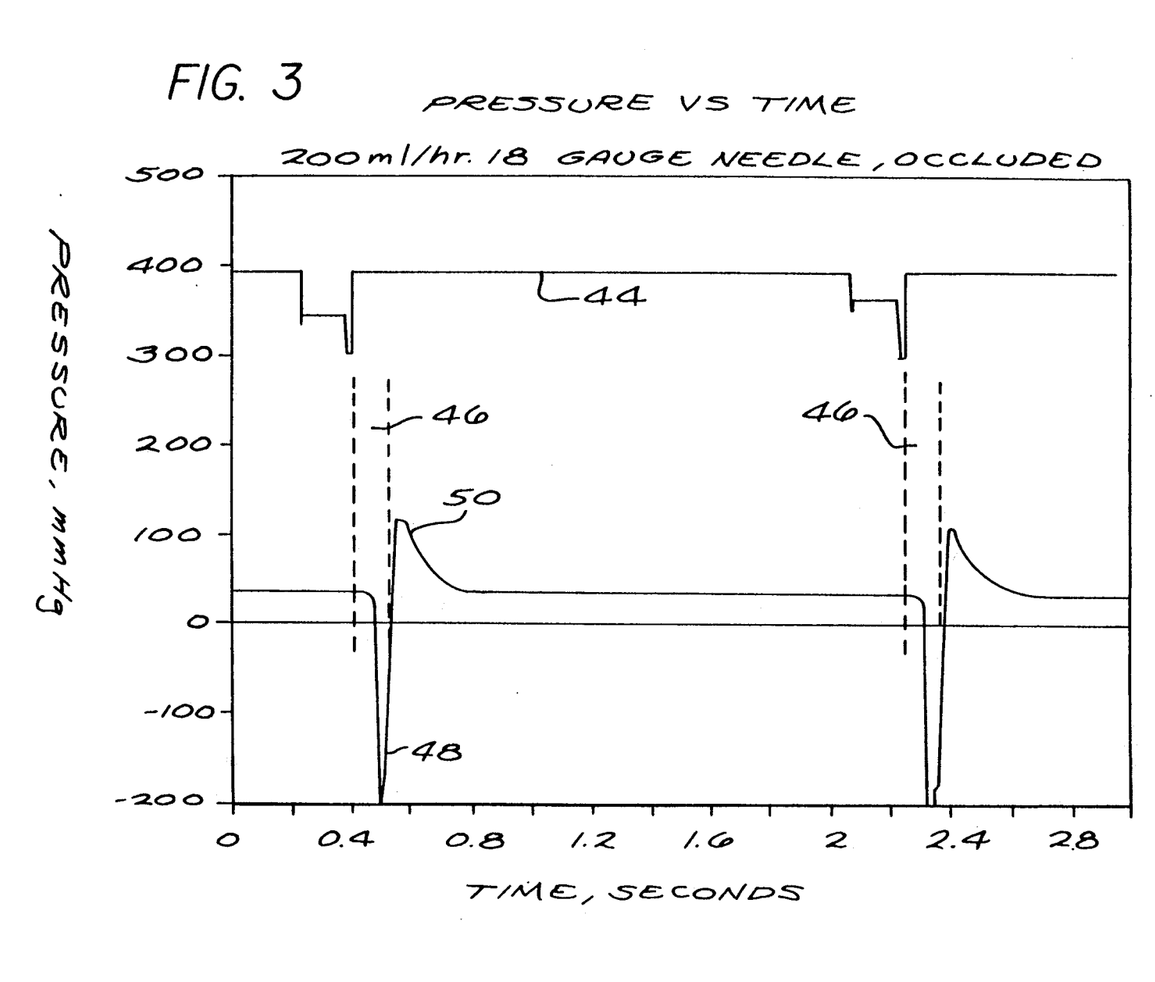
FIG. 3 illustrates a downstream pressure waveform with a total upstream occlusion.
Figure 4:
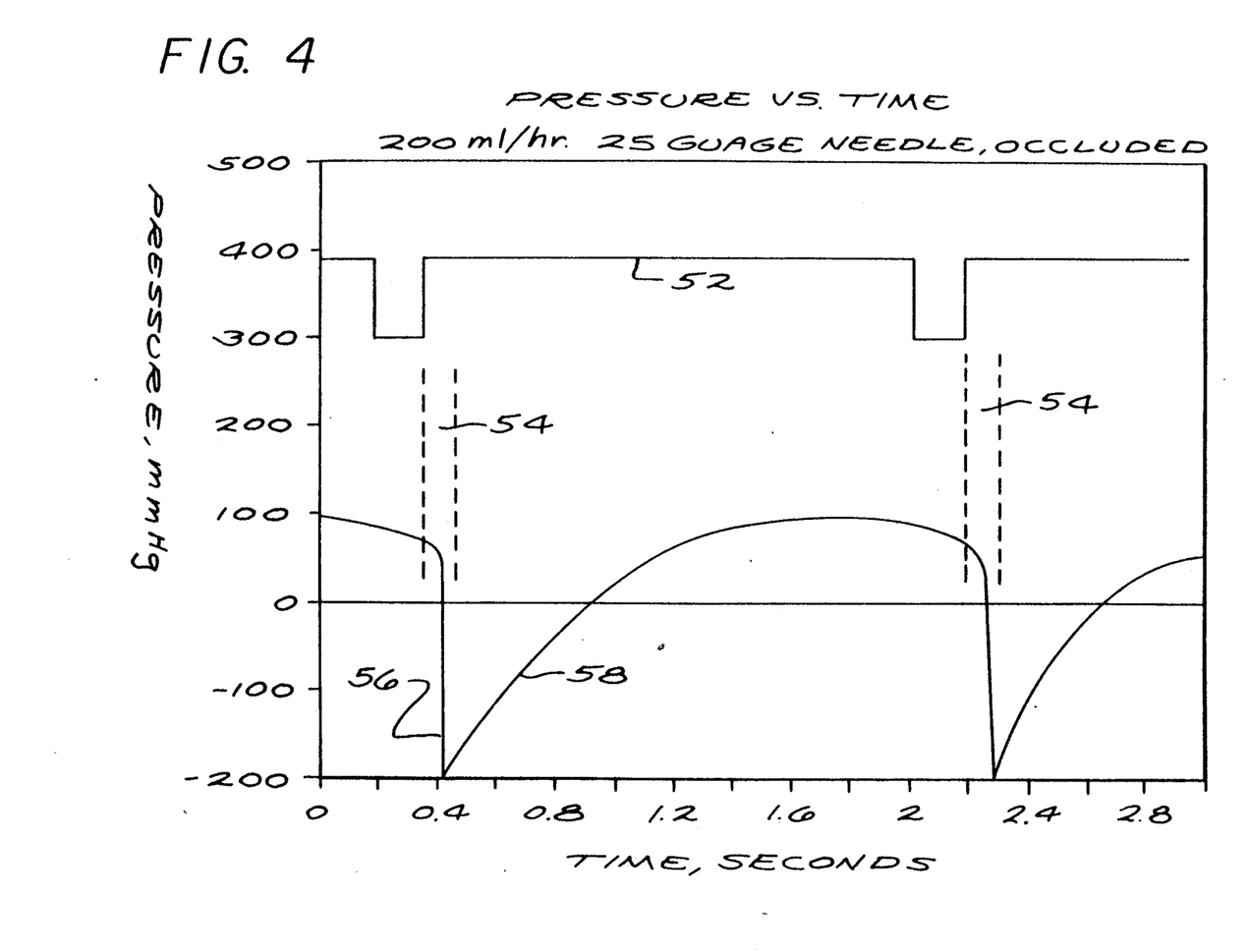
FIG. 4 illustrates another downstream pressure waveform similar to that of FIG. 3, with a total upstream occlusion.

A typical pressure waveform 22 resulting from an upstream occlusion during a flow transition period is illustrated in FIG. 2. The pressure at the beginning cycle is about 20 mmHg at point 24. At point 26 the most downstream finger opens the pumping segment of the tubing to the downstream side and the pressure at the transducer drops sharply. This all occurs within the detection window 30 within the flow transition period 28. The pressure drops from the starting pressure 32 during the pressure transient 34 down to the bottom pressure 36. Fluid begins to flow back during the recovery 38, filling the collapsed pumping segment of the tubing, resulting in the high pressure point or overshoot at 40, followed by the equalization of pressure at 42. A typical pressure waveform with a total upstream occlusion using a large, lower resistance, metal cannula terminating in a patient line is illustrated in FIG. 3. Superimposed on the chart is the signal from a rotation flag sensor 44. As in FIG. 2, the flow transition period 46 begins at the positive going edge of this signal, which coincides with the flag of the rotation flag sensor no longer being detected by a photosensor associated with the rotation flag sensor. When a negative-going pressure transient 48 occurs during the detection window, the positive-going pressure overshoot transient 50 again follows, as before. FIG. 4 represents a similar pressure waveform for the same condition with a smaller diameter cannula. The rotation flag sensor timing 52 also marks the beginning of the flow transition period 54, during which the negative-going pressure transient 56 occurs, again followed by the recovery 58. In both FIG. 3 and FIG. 4 two negative-going pressure transients are shown. It is apparent that the pressure between the flow transition periods is somewhat positive in each case. The pressure falls sharply when the pump tubing opens to the pressure sensor. An important feature of this negative-going pressure transient is an extremely short fall time. The pressure change occurs in less than three sampling periods (15 msecs.) which helps to discriminate against artifact transients because other pressure transients do not change this quickly. Variance in the duration of the negative transient between FIG. 3 and FIG. 4 is caused by the termination of the tubing with different cannula or needle sizes. The lower resistance cannula allows fluid to flow back into the pump tubing much faster, enabling the pressure to equalize in a shorter time.

Figure 5:
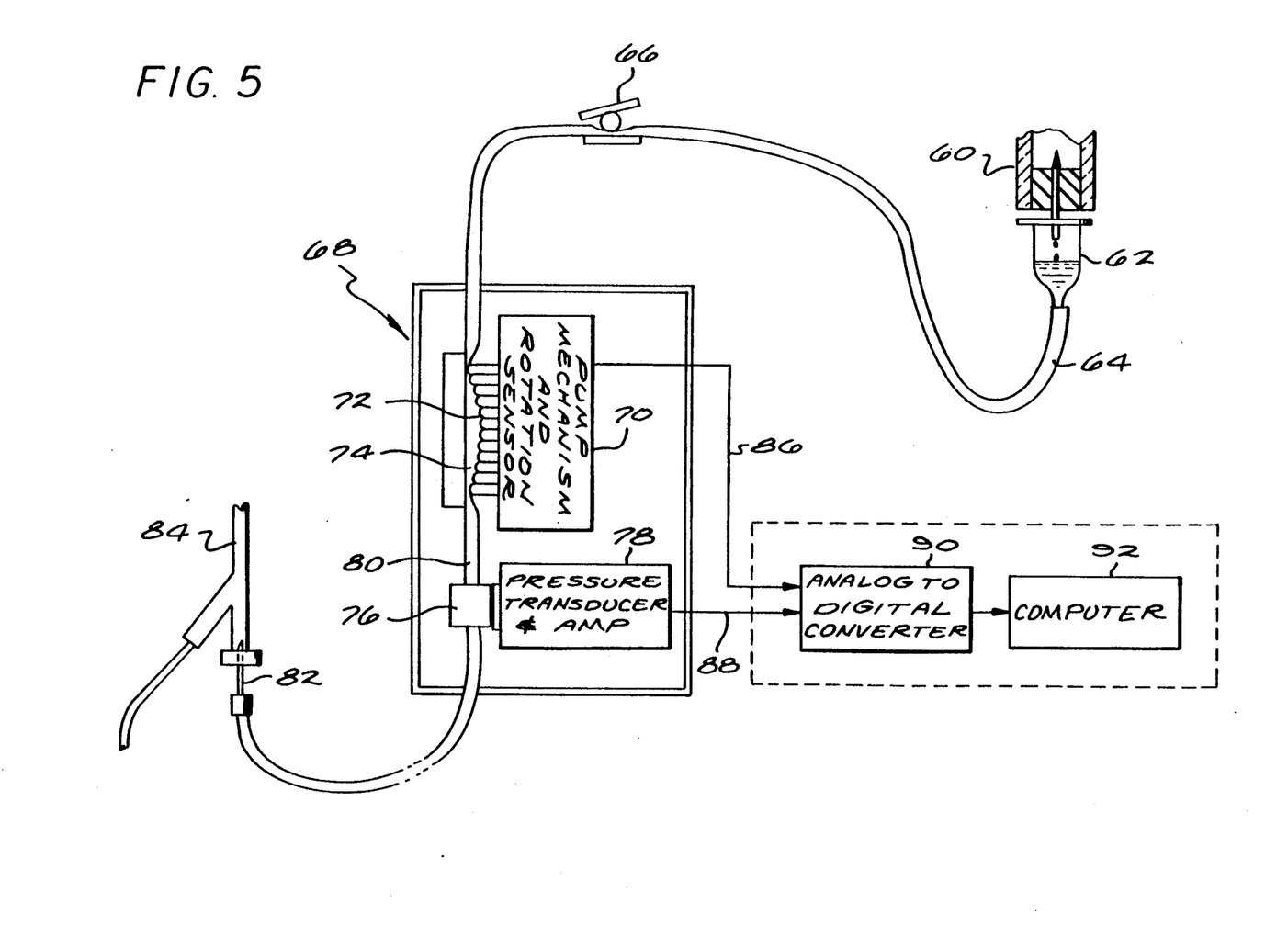
FIG. 5 is a schematic diagram of an IV administration set and a system for detecting an upstream occlusion in accordance with the invention.

A typical system setup for occlusion sensing is illustrated in FIG. 5. A conventional intravenous fluid bottle 60 is connected with an IV spike and drip chamber 62 through the upstream IV tubing 64 and IV tubing clamp 66 to the peristaltic pump mechanism 68. The peristaltic pump includes the peristaltic pump mechanism and rotation sensor 70, associated with the peristaltic fingers 72, which press upon the fluid line pumping segment 74 placed adjacent the fingers to cause fluid to flow through the line. A convenient placement for the pressure sensor module 76 and the pressure transducer 78 is immediately downstream of the pumping mechanism, within the housing of the peristaltic pump. A pressure transducer with negative pressure sensing capability to about −200 mmHg (gauge) is preferred. The downstream tubing 80 includes a cannula or needle 82 at its distal end, suitable for placement in vein of a patient, or in a vein simulator 84, which was used for testing purposes. A rotation sensor signal line 86 carries the rotation sensor signal from the pump and rotation sensor mechanism to an analog to digital converter 90, which is also connected with the pressure signal line 88 to the pressure transducer to receive and digitize the pressure signal as a series of discrete digitized samples, for determination of a downstream pressure parameter by a signal processing unit 92.

The pump rate was found to have an effect on the vacuum being generated with a partial upstream occlusion. With any given fluid resistance upstream the vacuum will be essentially proportional to the pump rate. This means, that in cases of partial upstream occlusion, at low rates a higher upstream fluid resistance will be tolerated than at high pump rates before an occlusion is detected.

The termination resistance (R) of the patient tubing affects the waveform of the speedup pressure transient. Tests were performed with large, low resistance cannula (R=14 mmHg/liter/hr), a small cannula higher resistance (R=550 mmHg/liter/hr), and a narrow lumen infusion catheter (R=1000 mmHg/liter/hr). The fall time and amplitude of the negative-going transient were practically unaffected by the terminating resistance. However, the recovery to the static pressure is strongly dependent on cannula size, and was found to take longer with a higher flow resistance (FIG. 3 and 4).

The range of −2 to +10 psi (−100 to +500 mmHg) was considered a practical operating region for detecting upstream occlusion conditions. The full range was tested with large and small needle sizes, both occluded and not occluded upstream. A static negative pressure of −100 mmHg takes into account that the pump may be located up to 4 feet above the IV site. The positive pressure is the maximum operating pressure of the pump without going into high pressure alarm.

While not intending to be bound by theory, it is believed that the pressure transient amplitude vs. the upstream minus downstream pressure difference appears to be a linear function of this pressure differential. The transient amplitude is about 40% of the pressure differential and is independent of needle size. With an occlusion that reduces the flow rate to 50% of the selected rate the pressure transient amplitude is almost as high as with a total occlusion (zero flow rate). A typical infusion pump drop rate detector design detects an upstream occlusion when the drop rate is 50% of the selected rate.

The volume of fluid between the pump and the occlusion will affect the amount of fluid that has to be pumped before the negative pressure transient will become large enough to be detected. The rate at which this negative pressure waveform builds up is also dependent on the volume and elasticity of the tubing between the pump and the occlusion. The larger and softer that the tubing is the more fluid will have to be pumped for a given negative pressure waveform.

The number of pump rotations necessary for the pressure transient to reach the full amplitude was measured using a standard Ivac infusion set with about 24 inches of vinyl tubing between the drip chamber and the pump. With the occlusion near the pump it takes about ½ rotation, and with the occlusion near the drip chamber it takes about two rotations for the pressure transient to become full size. The fact that it takes two rotations of the pump mechanism before the full amplitude appears does not mean that the whole amount of fluid is not being delivered to the patient (0.2 ml). The pressure transient amplitude has been found to increase much faster than the pump rate drops off. As an example, when the pressure transient size has reached 50% (110 mmHg) of the final transient size (220 mmHg) the pump rate has only declined 15%. Fluid will still go to the patient while the vacuum is building up in spite of an upstream occlusion in the tubing.

Figure 6:
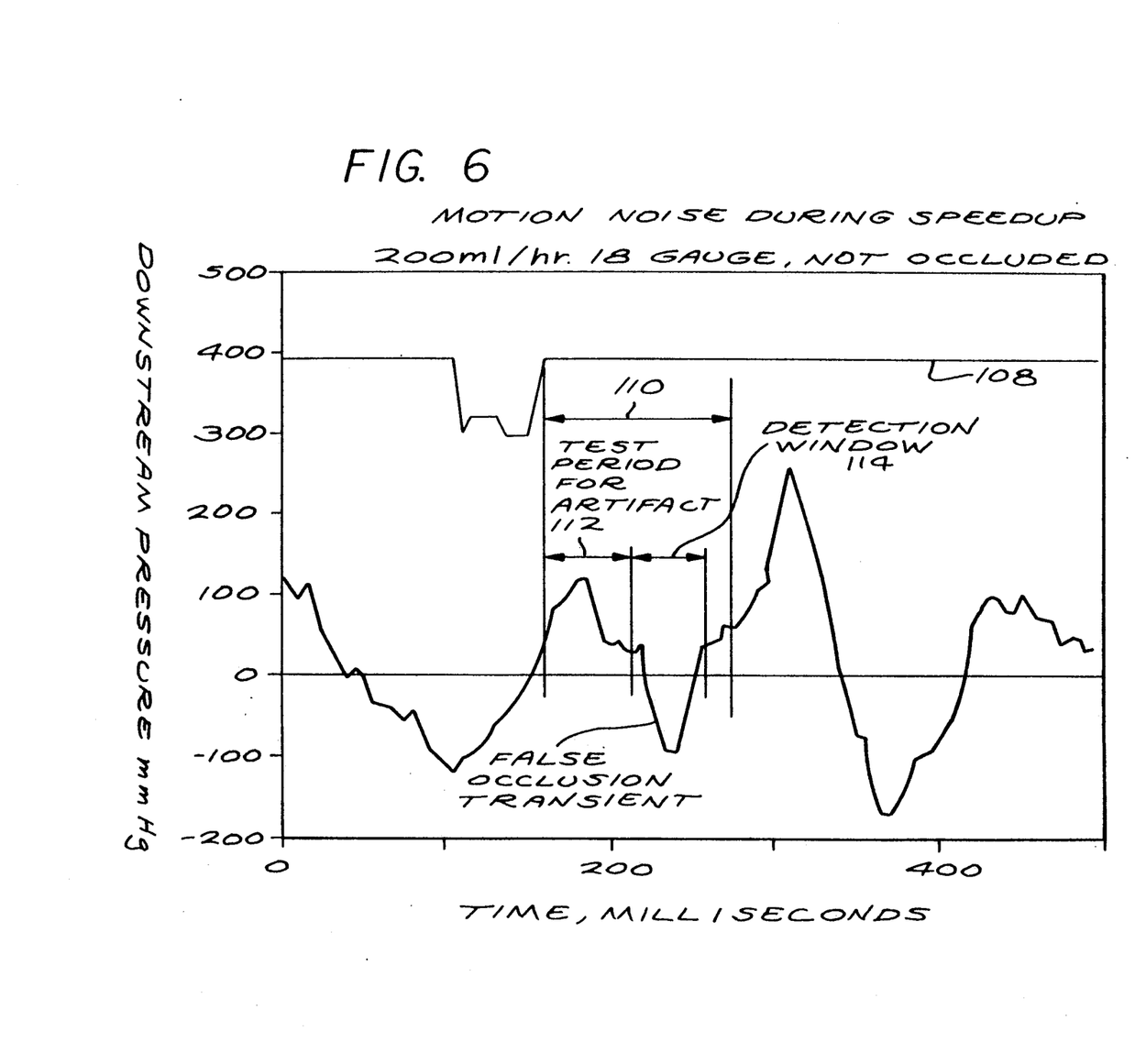
FIG. 6 illustrates a downstream pressure waveform showing an artifact occurring in the detection window.

FIG. 6 shows a time expanded view of an artifact which could produce a false occlusion alarm such as might occur due to patient motion occurring in the detection window. By monitoring the pressure from the start of the non-flow period 110 to the start of the detection window 114, artifacts may be identified. The pressure is fairly constant during this artifact testing time period 112 if no artifacts are present. However, if the pressure should change noticeably, an artifact condition would be suspected and an occlusion alarm could be inhibited. If this condition should exist for more than one or two speedup cycles in a row an alarm indicating the artifact condition could be given. Thus, the pressure measurement between the start of the non-flow period and the start of the detection window can be stored as a threshold value, to determine if a subsequent pressure value in this interval is greater than or equal to the suspected artifact pressure measurement. However, in the tests that were performed, the tubing needed to be struck very hard in order to interfere with the detection of an actual transient or cause a false alarm. This would probably not occur under normal conditions such as ambulation of the patient.

One currently preferred method for detecting upstream occlusions involves monitoring the difference in the pressure between two samples which are two sample periods apart (10 ms), and by measuring the pressure level at the start of the detection window and at the bottom of the pressure transient. Decisions will be based on these three values. The measurement of these values will only be performed during a short time period defining the detection window in the flow transition period of each duty cycle, from approximately 50 to 100 ms after the start of the flow transition period. These times are specific to the stepping rate of the IVAC 560 pump during the non-flow transition time and they would have to be modified depending on the actual step rate of the motor but in terms of the rotation sensor timing 108, the detection window should always be at the same number of motor steps after the rotation flag of the rotation sensor is no longer detected by the photo sensor. The actual location and width of the detection window may need to be adjusted for each particular type of pump and rotation sensor 108.

Figure 7:
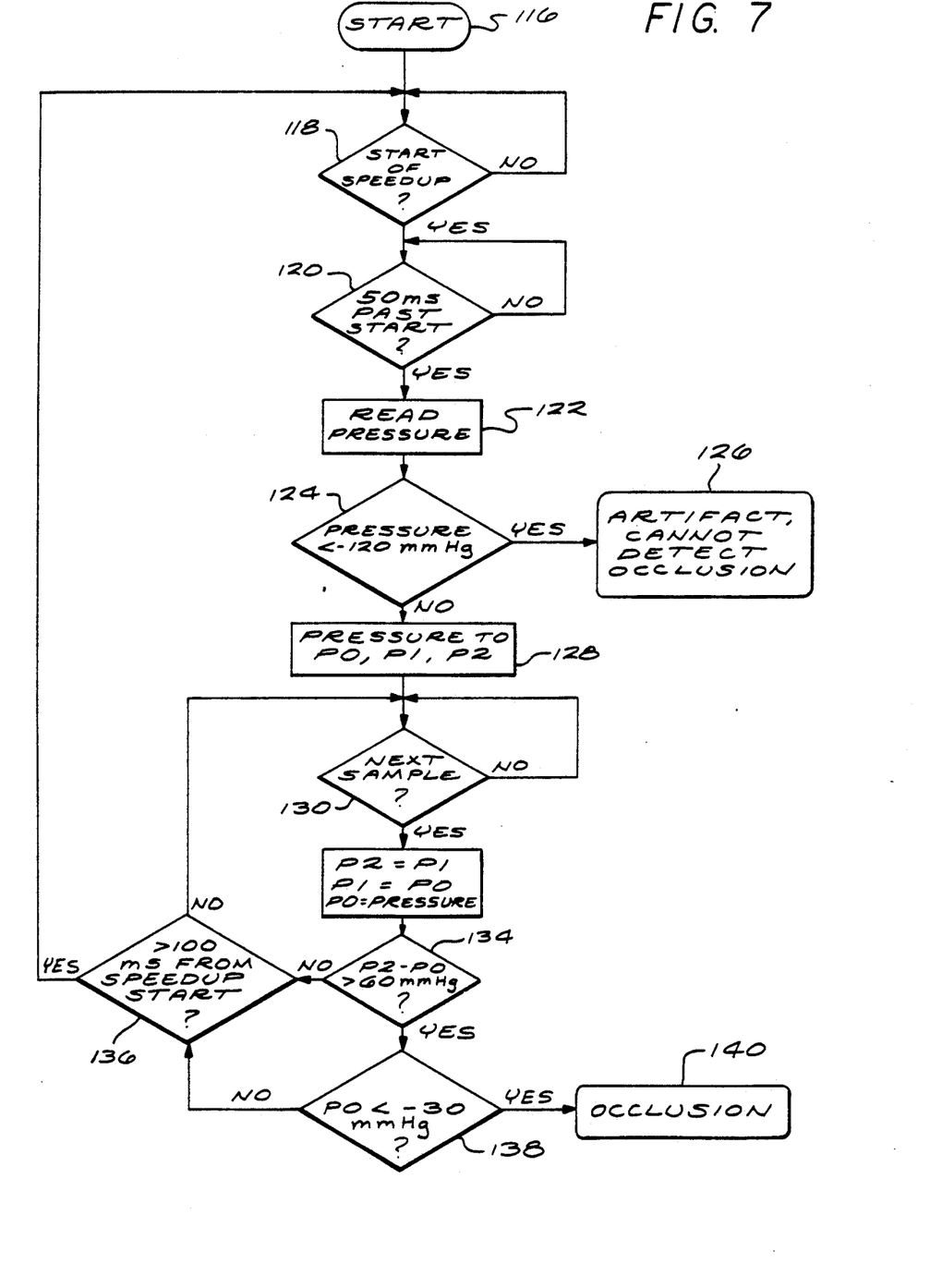
FIG. 7 is a flow chart showing pressure measurement steps of the preferred method embodiment of the invention.

FIG. 7 is a flow chart of the method, which was tested with recorded data. The operating range of the transducer was set to $-200$ to $+500$ mmHg. At the start 116 of the method, typically all values to be measured are initialized in a central processing unit, such as, for example, the Intel 85. During each cycle of the infusion pump, the start of the non-flow period 118 is determined based upon the tracking of the pump by the rotation sensor. When the start of the non-flow period is determined, a delay of 50 ms. past the start of the non-flow period may be used for detecting occlusion artifacts. After 50 ms., the first pressure measurement is taken 122, and compared at 124 with a threshold of $-120$ mm Hg., for example. If the measured pressure is less than the threshold, the extraordinary reading is determined at 126 to be an artifact, indicating an occlusion can not be reliably detected even if it is present. Otherwise, this first pressure reading is stored in memory locations $P_0$, $P_1$, and $P_2$ as is shown generally at 128. In another aspect of the method, a parameter of the stability of fluid pressure may be determined from pressure measurements taken from the start of the non-flow period during the 50 ms. delay. Such a parameter would be the root mean square of the pressure measurements during this delay interval, and if this root mean were to exceed a reference threshold value, an artifact condition would similarly be indicated.

During the first 50 milliseconds of the non-flow interval, the measured downstream pressure is not being influenced by the flow of fluid and has not yet reached the point at which the vacuum trapped between the upper and lower "fingers" is released. Therefore, this interval may be examined to determine if there is a large variation in pressure occurring due to vibration of the tubing or pressure variations caused by patient physiology (coughing, etc.) Such variations could reduce the effectiveness of the detection algorithm.

The pressure will be sampled a number (typically 10-20) of times depending on specifics of the mechanism. From these samples a calculation of signal variability will be made and compared with a threshold. A typical means to determine the variability is the calculation of Root Mean Square power in the signal. This RMS value is compared with a fixed threshold, and if the RMS value exceeds the threshold, then the measurement is not considered reliable and is not used for alarm purposes. Determination of the standard deviation of the pressure samples in this pre-transient period may also be used. Another method involves computing the sum of the absolute difference between successive samples of pressure over the interval. This value increases with short term variability just as does the AC RMS or standard deviation calculations but does not require the use of multiplication and therefore is more readily implemented in small microcomputers.

After the first sample is taken, at the beginning of the detection window, the system cycles at 130 to test whether the next sample period of 5 ms. has passed. After 5 ms., the value of $P_1$ is stored in the memory of the CPU as $P_2$, the value of $P_0$ is stored as $P_1$, and a new pressure reading of $P_0$ is taken. The difference between $P_2$ and $P_0$ is then compared at 134 with a difference threshold value of 60 mmHg, for example, and if the difference is greater than this 60 mmHg threshold, the value of $P_0$ is compared with a negative pressure threshold of $-30$ mmHg, for example, at 138 to determine whether there has been an occlusion 140. As an alternative, the slope of the pressure transient may be determined from one or more pairs of pressure samples, and compared with a slope threshold, to determine whether a sufficiently sharp negative-going transient has occurred to indicate upstream occlusion. The process of measuring and comparing the difference in pressure between two samples two sample periods apart can continue as long as the detection window, at 100 ms, has not ended, at 136. After 100 ms from the onset of the non-flow period, the detection window is closed, and the system cycles to test for the beginning of the next non-flow period at 118.

Figure 8:
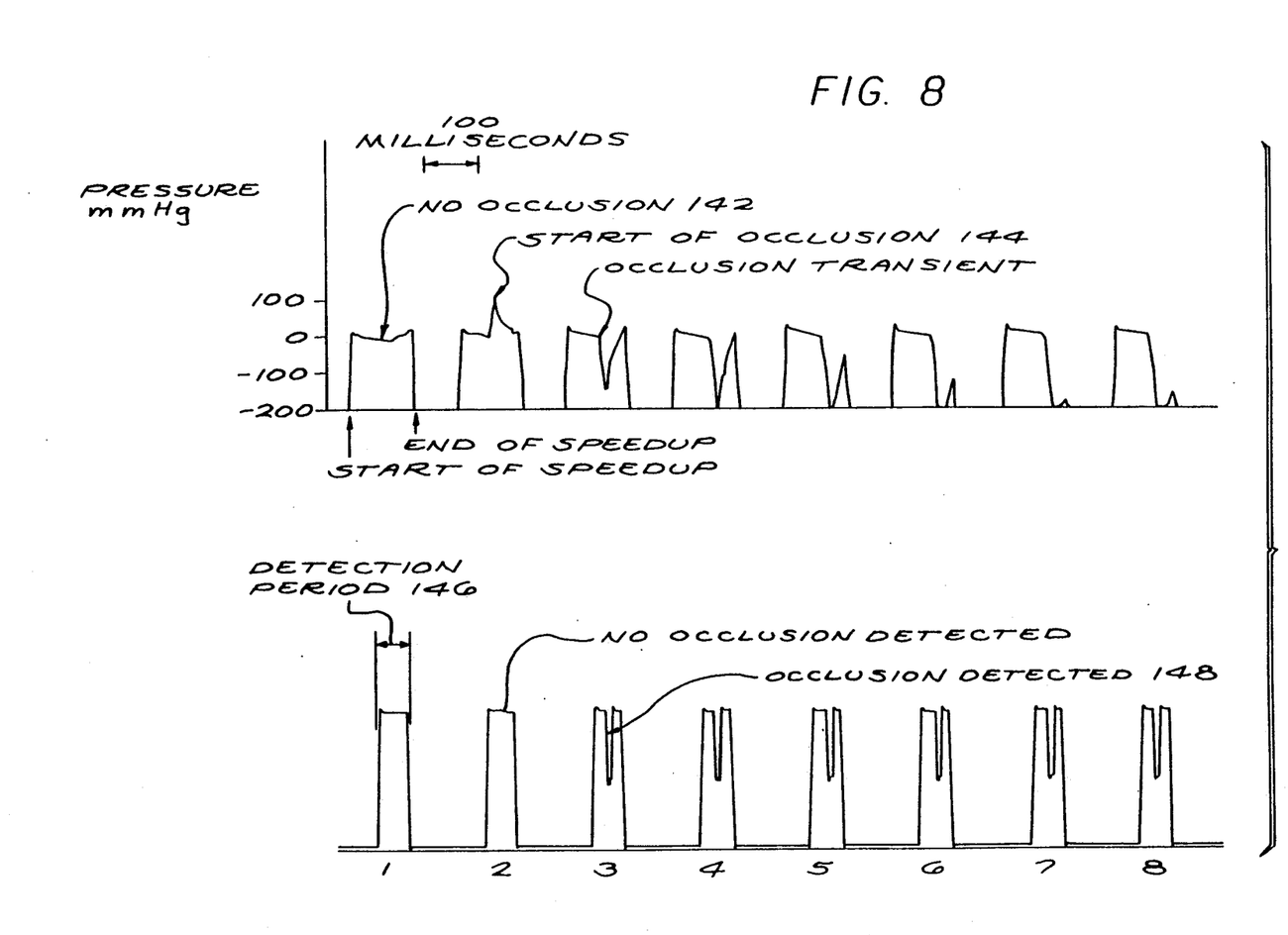
FIG. 8 illustrates strip chart recordings of a sequence of downstream pressure measurements during a series of pump duty cycles, with the upper chart illustrating downstream pressure, and the lower strip chart marking the time period of the detection window.

FIG. 8 shows a strip chart recording of a pressure waveform 142 in the upper channel of a sequence of snapshots of the downstream pressure during consecutive non-flow periods. The lower channel marks the detection "window" period (50 milliseconds). A negative-going marker in this time period indicates that an occlusion was detected. A positive-going marker at the beginning of the detection window 146 indicates that the transducer pressure was less than $-120$ mmHg at that moment making it impossible to detect a possible occlusion. This example shows the start of an occlusion 144. In the first non-flow period no transient appears. In the second, a small transient starts showing, but is not large enough to trigger the detection. In the third non-flow period, the transient 148 has grown large enough to be detected. In the following periods No. 4 to 8, the transient is larger and larger and will be detected every time.

Figure 9:
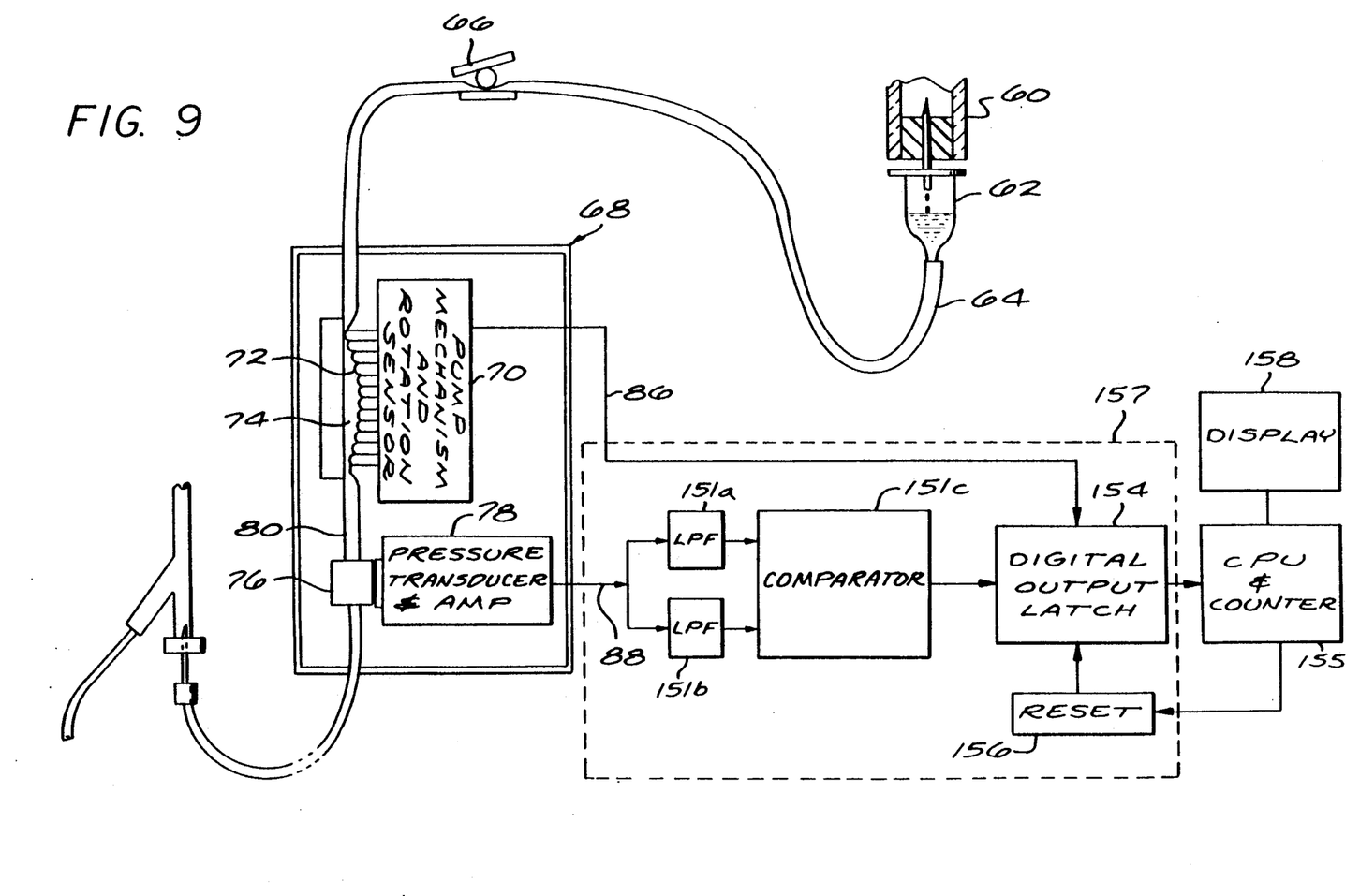
FIG. 9 is a schematic diagram of an IV administration set with another embodiment of an upstream occlusion monitoring system.

Another embodiment of an upstream occlusion detection system is illustrated in FIG. 9. This system is similar in most respects to the system shown in FIG. 5, and accordingly, like or corresponding elements bear like reference numerals. The principal difference in this upstream occlusion detection system is that the pressure signal is transmitted through a delta modulator circuit 157 detecting pressure signals within a frequency band of 5 to 30 Hz. The delta modulator circuit typically comprises a first low pass filter 151a, receiving the pressure signal via line 88, and functioning to prevent high frequency artifacts from corrupting the detection circuit function. The frequency characteristics of the low pass filter 151a are determined by the upper frequency boundary of the occlusion waveform spectrum, typically 20-30 Hz. A second low pass filter 151b, receives the pressure signal via line 88, and operates to provide an output which is essentially a time weighted average of the incoming signal. A comparator 151c receives output from both the first and second low pass filters. The comparator is one having hysteresis which compares the outputs of the first and second low pass filters, switching when the difference of the signals changes polarity. Typically this output changes on the positive-going rebound portion of the large transient pressure signal found during a non-flow period when an upstream occlusion exists. The circuit is therefore sensitive to changes in power in this frequency band, indicative of an upstream occlusion waveform occurrence. The digital output latch 154 detects the rising edge of the output of the comparator, and transmits a digital error signal to be counted by a central processing unit 155, which in turn executes the reset 156 of the digital output latch 154. The output of the latch is sampled by the central processing unit during the non-flow transition period. This limits interference from noise and artifacts. The upstream occlusion appears as a sharp negative-going pressure transient during the non-flow transition period, followed by a positive rebound pressure signal. Spectral analysis, such as by Fourier analysis of the pressure waveforms, indicates a noticeable power content increase in frequencies from 5 to 30 Hz during occlusion.

The low pass filters 151a, 151b, the comparator 151c and the latch 154 of the delta modulator 157 thus discriminate power in this frequency band. The output of the circuit changes a digital level based upon whether the power in the band exceeds the power threshold level, set by the hysteresis of the comparator. The central processing unit includes a counter, which is toggled by the output latch on the transition from low to high count detection, and which will indicate an error when the count exceeds a given threshold value, in the display 158, which may be a chart or a computer monitor, for example. The frequency band can be widened or narrowed, and a different frequency band for detection can be selected, such as from 40-50 Hz. Appropriate self-testing capability for calibration purposes may be added, for increased reliability of the system.

In another embodiment, the power in the frequency band of the pressure waveform may be determined by the central processing unit by determining the root mean square of the analog signal during the non-flow period, the sum of the sample pressure values minus a baseline or "starting" pressure, or otherwise determining an integral of the measured pressure values during the detection window, and displayed on a display unit 158.

Based upon the foregoing, it can be appreciated that the method and system for detecting occlusion in a fluid line upstream of a peristaltic pump in an intravenous fluid administration system provides for a simplified, low cost, way of monitoring upstream occlusion without the necessity of modification of existing peristaltic pump mechanisms. Placed in a downstream configuration, the system of the invention can be readily adapted to monitor upstream occlusion in existing peristaltic pump IV infusion systems.

Although specific embodiments of the invention have been described and illustrated, it is clear that the invention is susceptible to numerous modifications and adaptations within the ability of those skilled in the art and without the exercise of the inventive faculty. Thus, it should be understood that various changes in form, detail and uses of the present invention may be made without departing from the spirit and scope of the invention.

We claim:

1. A method for detecting an occlusion in a fluid line upstream of a pump adapted to cause fluid to flow from an upstream portion to a downstream portion of said fluid line, said pump having a duty cycle including a transition period in which fluid pressure is communicated from said upstream portion to said downstream portion of said fluid line, the steps of said method comprising:
   monitoring fluid pressure in said fluid line downstream of said pump during said transition period to detect the occurrence of a negative-going pressure waveform;
   determining the power content of said detected negative-going pressure waveform over a range of frequencies; comparing said power content with a predetermined power threshold; and
   generating an occlusion signal when said waveform power content exceeds said predetermined power threshold.

2. The method of claim 1, wherein said power content is determined from the root mean square of said negative-going pressure waveform over said range of frequencies.

3. The method of claim 1, wherein said range of frequencies is from about 5 to about 30 Hz.

4. The method of claim 1, wherein said power content is determined from a pressure-time integral of the negative-going pressure waveform with respect to a beginning baseline pressure.

5. A method for detecting an occlusion in a fluid line upstream of a pump adapted to cause fluid to flow from an upstream portion to a downstream portion of said fluid line, said pump having a cycle with a period during which fluid pressure is communicated from said upstream portion to said downstream portion of said fluid line, the steps of said method comprising:
   monitoring fluid pressure in said fluid line downstream of said pump during the period of said pump cycle during which fluid pressure is communicated from said upstream portion to said downstream portion to detect the occurrence of negative-going pressure in said fluid line; and
   generating a signal indicating an occlusion when negative-going pressure is detected.

6. The method of claim 5, wherein said signal indicating an occlusion is generated only when said negative-going pressure falls below a predetermined negative pressure threshold.

7. The method of claim 6, wherein said predetermined negative pressure threshold is −30 mmHg.

8. The method of claim 5, wherein said step of monitoring fluid pressure further comprises sampling said fluid pressure at a plurality of times to provide a plurality of pressure samples, determining the difference between two samples which are a predetermined time interval apart, and generating said occlusion signal when said difference is greater than a predetermined difference threshold.

9. The method of claim 8, wherein said difference threshold is about 60 mmHg for a predetermined time interval of about 10 ms.

10. The method of claim 5, further comprising the step of determining the slope and amplitude of said negative-going pressure, and generating said occlusion signal only when said slope is greater than a predetermined slope threshold and said negative-going pressure falls below a predetermined pressure threshold.

11. The method of claim 5, wherein said pump is a peristaltic pump operating on a pumping segment of said fluid line and having a plurality of occluding fingers which move fluid in a peristaltic manner.

12. The method of claim 11, wherein said fluid pressure is monitored during a detection window in each said period of said pump cycle when the most downstream peristaltic finger of said pump opens said pumping segment to the fluid line downstream of said pump.

13. The method of claim 5, further comprising the step of detecting an artifact condition by monitoring fluid pressure in said fluid line prior to said pump cycle period during which fluid pressure is communicated from said upstream portion to said downstream portion, comparing said monitored pressure to a predetermined artifact minimum pressure threshold and generating an artifact signal when said monitored pressure falls below said artifact threshold.

14. The method of claim 13, wherein the step of detecting said artifact condition comprises determining the amplitude and slope of said fluid pressure, and generating said artifact signal when either said amplitude falls below an artifact minimum pressure threshold, or said slope exceeds an artifact slope threshold.

15. The method of claim 13, further comprising the step of monitoring fluid pressure during said period in an interval of non-flow prior to communication of said fluid pressure from said upstream portion to said downstream portion of said fluid line, determining a parameter of the variability of fluid pressure during said interval, and generating an artifact signal when said parameter of variability of fluid pressure exceeds a predefined threshold.

16. The method of claim 5, further comprising the step of detecting an artifact condition by monitoring fluid pressure in said fluid line prior to said pump cycle period during which fluid pressure is communicated from said upstream portion to said downstream portion, comparing said monitored pressure to a predetermined artifact minimum pressure threshold and inhibiting the generation of said occlusion signal when said monitored pressure falls below said artifact threshold.

17. The method of claim 5, wherein said negative-going pressure has a waveform comprising a range of frequencies, and further comprising the steps of determining the power content of said negative-going pressure detected over a range of frequencies, comparing said power content with a power content threshold, and generating said occlusion signal when said power content exceeds said power content threshold.

18. The method of claim 17, wherein said power content is determined from the root mean square of said negative-going pressure waveform over said range of frequencies.

19. The method of claim 17, wherein said range of frequencies is from about 5 to about 30 Hz.

20. The method of claim 17, wherein said power content is determined from a pressure-time integral of the negative-going pressure waveform with respect to a beginning baseline pressure.

21. A system for detecting an occlusion in a portion of a fluid line upstream of a pump, the pump being adapted to cause fluid to flow from the upstream portion to a downstream portion of said fluid line, said pump having a cycle with a period during which fluid pressure is communicated from said upstream to said downstream portion of said fluid line, the system comprising:

means for monitoring fluid pressure in said fluid line downstream of said pump during the period of said pump cycle during which fluid is communicated from said upstream portion to said downstream portion to detect the occurrence of negative-going pressure in said fluid line; and means for generating a signal indicating an occlusion in said upstream portion of the fluid line when negative-going pressure is detected by said means for monitoring.

22. The system of claim 21, wherein said signal indicating an occlusion is generated only when said negative-going pressure falls below a predetermined negative pressure threshold.

23. The system of claim 21, wherein said means for monitoring fluid pressure further comprises means for sampling said fluid pressure at a plurality of times to provide a plurality of pressure samples, means for determining the difference between two samples which are a predetermined time interval apart, and means for generating said occlusion signal when said difference is greater than a predetermined difference threshold.

24. The system of claim 21, further comprising means for determining the slope and amplitude of said negative pressure, and means for generating said occlusion signal only when said slope is greater than a predetermined slope threshold and said negative-going pressure falls below a predetermined pressure threshold.

25. The system of claim 21, wherein said pump is a peristaltic pump operating on a pumping segment of said fluid line and having a plurality of fingers which move fluid in a peristaltic manner.

26. The system of claim 25, wherein said fluid pressure is monitored during a detection window in each said period of said pump cycle when the most downstream peristaltic finger of said pump opens said pumping segment to the fluid line downstream of said pump.

27. In an intravenous fluid administration system including a fluid line, and a pump adapted to cause fluid to flow from an upstream portion to a downstream portion of said fluid line, said pump having a duty cycle with a cyclical flow transition period during which fluid pressure is communicated downstream to induce a negative pressure transient downstream of said pump when an occlusion exists in said fluid line upstream of said pump, an upstream occlusion detection system comprising the combination of:

a pressure detector for measuring fluid pressure in said fluid line at a location downstream of said pump;

means for monitoring said fluid pressure in said fluid line downstream of said pump during said flow transition period to detect the occurrence of each negative pressure transient; and means for generating an occlusion signal indicating an occlusion condition upstream of said pump when a said negative pressure transient is detected.

28. The combination of claim 27, further comprising means for determining the amplitude of each negative-going pressure transient, and said occlusion signal generating means being operative to generate said occlusion signal only when said amplitude falls below a minimum pressure threshold.

29. The combination claim 27, wherein said means for monitoring said fluid pressure further comprises means for providing a plurality of pressure samples, means for determining the difference between two samples a predetermined time interval apart for at least one pair of said pressure samples, and said means for generating said occlusion signal being operative to generate said occlusion signal when said difference is greater than a predetermined difference threshold.

30. The combination of claim 27, further comprising means for determining the slope and amplitude of each said negative pressure transient, and said means for generating said occlusion signal being operative to generate said occlusion signal only when said slope is greater than a predetermined slope threshold and said amplitude falls below a predetermined minimum pressure threshold.

31. The combination of claim 27, further comprising means for detecting an artifact condition by monitoring fluid pressure in said fluid line prior to said pump cycle period during which fluid pressure is communicated from said upstream portion to said downstream portion, means for comparing said monitored pressure to a predetermined artifact minimum pressure threshold and means for generating an artifact signal when said monitored pressure falls below said artifact threshold.

32. The combination of claim 27, further comprising means for detecting an artifact condition by monitoring fluid pressure in said fluid line prior to said pump cycle period during which fluid pressure is communicated from said upstream portion to said downstream portion, means for comparing said monitored pressure to a predetermined artifact minimum pressure threshold and means for inhibiting the generation of said occlusion signal when said monitored pressure falls below said artifact threshold.

33. The combination of claim 27, wherein each negative pressure transient has a waveform over a range of frequencies, and further comprising means for determining power content of each said negative pressure transient detected over a range of frequencies, means for comparing said power content with an power threshold, and said means for generating said occlusion signal being operative to generate said occlusion signal only when said power content exceeds said power threshold.

34. In a system for detecting an occlusion in a fluid line upstream of a pump wherein the pump operates on said fluid line to cause fluid to flow from an upstream portion to a downstream portion of said fluid line, said pump having a cycle with a non-flow transition period during which fluid pressure is communicated from said upstream portion to said downstream portion of said fluid line, the combination comprising:
   means for monitoring fluid pressure in said fluid line downstream of said pump during said non-flow transition period to detect the occurrence of a negative-going pressure transient; and
   means for determining power content over a range of frequencies of each said negative-going pressure transient detected by said means for monitoring, comparing said power content with a power threshold, and generating an occlusion signal when said power content exceeds said power threshold.

* * * * *

UNITED STATES PATENT AND TRADEMARK OFFICE
CERTIFICATE OF CORRECTION

PATENT NO. : 5,096,385
DATED : March 17, 1992
INVENTOR(S) : Georgi et al.

It is certified that error appears in the above-identified patent and that said Letters Patent is hereby corrected as shown below:

IN THE CLAIMS:

Column 12, lines 59-60, change "negative-going" to --negative--.

Signed and Sealed this

First Day of June, 1993

Attest:

MICHAEL K. KIRK

*Attesting Officer*      *Acting Commissioner of Patents and Trademarks*